(12) United States Patent
Roxhed et al.

(10) Patent No.: US 10,433,766 B2
(45) Date of Patent: Oct. 8, 2019

(54) MINIATURIZED FLUID FLOW REGULATING DEVICE

(71) Applicant: Aerocrine AB, Solna (SE)

(72) Inventors: Niclas Roxhed, Bromma (SE); Göran Stemme, Lidingö (SE); Staffan Johansson, Bro (SE)

(73) Assignee: CIRCASSIA AB, Uppsala (SE)

( * ) Notice: Subject to any disclaimer, the term of this patent is extended or adjusted under 35 U.S.C. 154(b) by 631 days.

(21) Appl. No.: 15/111,888

(22) PCT Filed: Jan. 23, 2015

(86) PCT No.: PCT/EP2015/051340
§ 371 (c)(1),
(2) Date: Jul. 15, 2016

(87) PCT Pub. No.: WO2015/110572
PCT Pub. Date: Jul. 30, 2015

(65) Prior Publication Data
US 2016/0338619 A1    Nov. 24, 2016

(30) Foreign Application Priority Data
Jan. 24, 2014    (SE) ..................................... 1450070

(51) Int. Cl.
*A61B 5/08*    (2006.01)
*A61B 5/097*    (2006.01)
(Continued)

(52) U.S. Cl.
CPC .............. *A61B 5/097* (2013.01); *A61B 5/082* (2013.01); *G05D 7/012* (2013.01); *G05D 7/0113* (2013.01);
(Continued)

(58) Field of Classification Search
CPC ........ G05D 7/012; G05D 7/01; G05D 7/0113; G05D 7/0173; A61B 5/097; A61B 5/08;
(Continued)

(56) References Cited

U.S. PATENT DOCUMENTS 3,057,373 A * 10/1962 Bragg .................... B64D 13/02
137/460
3,523,559 A * 8/1970 Gibson .................. G05D 7/012
137/517
(Continued)

FOREIGN PATENT DOCUMENTS

CA    1121249 A1    4/1982
EP    0828101 A1    3/1998
(Continued)

OTHER PUBLICATIONS

Office Action from corresponding Japanese Application No. 2016-548173, dated Oct. 12, 2018.
(Continued)

*Primary Examiner* — Eric J Messersmith
(74) *Attorney, Agent, or Firm* — Tucker Ellis LLP

(57) ABSTRACT

The invention relates to a miniaturised fluid flow regulating device comprising a fluid flow channel with an inlet portion, an outlet portion and a flow regulation passage between the inlet portion and the outlet portion, an elongated beam element arranged in the flow channel, such that a pressure difference over the inlet portion and the outlet portion causes the beam element to bend and regulate fluid flow in the flow regulation passage. The invention further relates to a breath analysis device comprising such a flow regulating device for regulating a flow of exhaled breath.

14 Claims, 4 Drawing Sheets

(51) Int. Cl.
*G05D 7/01* (2006.01)
*A61M 15/00* (2006.01)
*A61M 16/08* (2006.01)

(52) U.S. Cl.
CPC ......... *G05D 7/0173* (2013.01); *A61M 15/002* (2014.02); *A61M 16/085* (2014.02); *A61M 2205/3334* (2013.01); *A61M 2230/437* (2013.01)

(58) Field of Classification Search
CPC ............ A61B 5/082; A61M 2230/437; A61M 15/002; A61M 16/085; A61M 2205/3334
See application file for complete search history.

(56) References Cited

U.S. PATENT DOCUMENTS

| | | | | |
|---|---|---|---|---|
| 3,646,970 | A * | 3/1972 | Romanowski | H01H 35/242 137/468 |
| 4,230,149 | A * | 10/1980 | Worthen | A01G 25/16 137/504 |
| 5,163,920 | A * | 11/1992 | Olive | A61M 5/14276 128/DIG. 12 |
| 5,582,210 | A * | 12/1996 | Bartholomew | G05D 7/0106 138/45 |
| 5,727,546 | A * | 3/1998 | Clarke | A61M 15/0028 128/203.15 |
| 8,167,002 | B2 * | 5/2012 | Kuhne | G05D 7/012 137/504 |
| 8,998,838 | B2 * | 4/2015 | Yalamanchili | A61F 9/00781 604/8 |
| 9,752,692 | B2 * | 9/2017 | Abouelleil | F16K 15/031 |
| 2002/0182091 | A1 | 12/2002 | Potter | |
| 2008/0000539 | A1 * | 1/2008 | Bivin | G05D 7/012 138/46 |
| 2012/0103453 | A1 * | 5/2012 | Buseyne | F16K 1/22 138/46 |
| 2015/0265184 | A1 * | 9/2015 | Wondka | A61B 5/082 600/532 |

FOREIGN PATENT DOCUMENTS

| | | |
|---|---|---|
| WO | 79/01092 A1 | 12/1979 |
| WO | 9214199 A1 | 8/1992 |
| WO | 95/05208 A1 | 2/1995 |
| WO | 2006080885 A1 | 8/2006 |
| WO | 2008016698 A2 | 2/2008 |
| WO | 2014007659 A1 | 1/2014 |

OTHER PUBLICATIONS

International Search Report from corresponding International Patent Application No. PCT/EP2015/051340, dated May 29, 2015.

* cited by examiner

MINIATURIZED FLUID FLOW REGULATING DEVICE

TECHNICAL FIELD

The present invention relates generally to a miniaturized fluid flow regulating device, the use of such a fluid flow regulating device in a breath analysis device and a method of fabricating such a fluid flow regulating device

BACKGROUND ART

Exhaled breath diagnostics as a clinical method is reaching more and more acceptance in a variety of different diseases. To ensure reproducible measurement results, exhaled breath from patients should conform to certain protocols dictating the physical parameters (e.g. flow rate, pressure, temperature etc.) under which the test should be made. Thus it is sought to perform measurements under substantially constant flow of exhaled breath, despite variations in applied pressure.

In WO 2006/080885 A1 a constant flow regulator device for maintaining a constant flow of fluid is disclosed. The device comprises an inlet duct for incoming fluid, a housing, and a movable partition facing the inlet duct and being subjected to an elastic force. A fluid passage of variable cross section area is formed between the inlet duct and the movable partition. The housing and movable partition form an inner compartment in fluid communication with the inlet duct for establishing a fluid pressure inside the inner compartment approximately equal to the fluid pressure in the inlet duct. The size of the movable partition is significantly greater than the size of the inlet duct such that, in use, the partition is moved towards the inlet duct against the elastic force when the fluid pressure in the inlet duct increases to reduce said fluid passage cross section area, and vice versa, thereby maintaining constant fluid flow.

WO 9505208 discloses a device for the administration of an inhalation medicament, including a body defining a through-going air pathway having a longitudinal axis, an air inlet, an air outlet forming a mouthpiece, means for dispensing medicament into the pathway and air flow regulating means, characterised in that the air flow regulating means includes a movable obstructing means adapted to reduce the cross-sectional area of the pathway at a location between the air inlet and the means for dispensing medicament, and biasing means, whereby the obstructing means is biased into a first resting position in which the cross-sectional area of the pathway is minimum and is adapted to move against the bias of the biasing means to a second position in which the cross-sectional area of the pathway is maximum in response to a pressure fall at the mouthpiece caused by inhalation and is adapted to move further to a third position in which the cross-sectional area of the pathway is less than maximum in response to a greater pressure fall at the mouthpiece caused by inhalation WO 2008016698 discloses a fluid flow regulating mechanism designed particularly for use in connection with aerosolized drug delivery devices is disclosed. The mechanism includes a housing, planar elastic element, regulating element and positioning component. The elements of the device are configured in a manner such that a flow channel through the housing is opened or closed depending on the flow rate of fluid through a flow channel.

WO 9214199 discloses flow regulating device placed in a fluid path to passively compensate the fluctuations in the fluid pressure by deflection or displacement.

The current trend towards handheld point-of-care devices has brought a need for miniaturized flow handling systems. The previously disclosed device requires a significant size of the partition. It is therefore desired to find alternative solutions to the problem of regulating a fluid flow that may be suitable for miniaturisation, and that still may be used to regulate the relatively large flows of exhaled breath. For example, in asthma monitoring (fractional exhaled NO, FENO), regulatory guidelines dictates that measurements of nitric oxide concentration should be made at an exhaled flow rate of 50±5 ml/s ("ATS/ERS recommendations for standardized procedures for the online and offline measurement of exhaled lower respiratory oxide and nasal nitric oxide", 2005. Am. J. Respir. Crit. Care. Med. 2005; 171: 912-930).

SUMMARY OF INVENTION

An object of the present invention is to reduce the shortcomings of the above mentioned devices.

In particular it is an object of the present invention to provide a fluid flow regulating device which may be integrated in handheld analysis devices. It is further an object to provide a fluid flow regulating device which is able to passively regulate a comparatively large fluid flow in relation to its size. It is also sought to provide a fluid flow regulating device which may be produced at a reduced cost.

In a first aspect there is provided a miniaturised fluid flow regulating device 1 comprising a fluid flow channel 2 with an inlet portion 3, an outlet portion 4 and a flow regulation passage 5 between the inlet portion and the outlet portion, an elongated beam element 10 arranged in the flow channel, such that a pressure difference over the inlet portion and the outlet portion causes the beam element to bend and regulate fluid flow in the flow regulation passage, wherein the elongated beam has a first end portion 13 and a second end portion 14 and extends from the inlet portion to the outlet portion of the flow channel, wherein the device comprises supporting means 19a, 19b, 20a, 20b, and wherein at least one of the first and second end portions are supported in the device by the supporting means.

In a second aspect there is provided a breath analysis device comprising a miniaturised flow regulating device as described above for regulating a flow of exhaled breath to maintain a flow in the range of 10-300 ml/s, preferably maintaining a flow of 50±5 ml/s, and preferably over a pressure range of 1000 Pa.

In a third aspect there is provided use of a miniaturised fluid flow regulating device as described above in a breath analysis device for regulating a flow of exhaled breath to maintain a flow in the range of 10-300 ml/s, preferably maintaining a flow of 50±5 ml/s, and preferably over a pressure range of 1000 Pa.

Thus the invention relates to a miniaturised fluid flow regulating device comprising a fluid flow channel with an inlet portion, an outlet portion and a flow regulation passage between the inlet portion and the outlet portion, an elongated beam element arranged in the flow channel, such that a pressure difference over the inlet portion and the outlet portion causes the beam element to bend and regulate fluid flow in the flow regulation passage.

Thereby a simple fluid flow regulating device is achieved which may be produced at a reduced cost and integrated in handheld analysis devices. It is able to passively regulate a comparatively large fluid flow in relation to its size.

The elongated beam may comprise a first and a second face, and wherein the first face is subjected to fluid pressure communicating with the inlet portion of the fluid flow channel, such that a pressure difference acting on the first and a second face of the elongated beam causes the beam element to bend and regulate fluid flow in the flow regulation passage.

Thereby the regulation may be achieved by simple means, to efficiently provide passive self-adjusting flow regulation where the spring force in the beam is balancing the pressure difference over the beam.

The device may comprise a fluid space separated from the flow channel, communicating with the inlet portion of the fluid flow channel, and wherein the first face of the elongated beam defines a wall in the fluid space. Thereby the pressure at the inlet portion may be used to deflect the beam to regulate the flow.

The elongated beam may be arranged such that there are leak passages formed from the fluid space separated from the flow channel, to lead fluid from the fluid space towards the outlet portion.

The leak passages may be minimised or configured to provide a certain leak flow characteristic.

The second face may define a wall in the flow regulation passage. Thereby the bending of the beam may directly regulate the flow in the flow regulation passage.

The flow regulation passage may be configured to provide a pressure drop from the inlet portion to the outlet portion of the fluid flow channel. Thereby a pressure difference is achieved over the inlet and outlet portion, and thus over the elongated beam element.

The elongated beam may be arranged having the direction of elongation along the fluid flow channel. Thereby a bending of the beam may cause a uniform regulation of the cross-sectional area of the flow regulation passage.

The elongated beam has a first end portion and a second end portion and extends from the inlet portion to the outlet portion of the flow channel.

The first end portion of the elongated beam may be supported in the device. The first end portion may be clamped in the device, whereby the elongated beam forms a cantilever. The second end portion may be free. Thus a large deflection of the beam may be achieved.

The first end portion of the elongated beam may be directed towards the outlet portion of the fluid flow channel. Thus the fluid space may be defined by the attachment of the first end portion in the device.

The second end portion may be supported in the device, thus e.g. increasing the resonance frequency of the beam.

The device comprises supporting means, and wherein at least one of the first and second end portions are supported in the device by the supporting means. By providing simple support, a larger deflection of the beam may be achieved for a given pressure difference.

The supporting means may be configured to provide support along the whole length of the simply supported end portion(s), at an intermediate position along the length of the simply supported end portion(s) and/or at the corners of the end portion(s). Thereby the support means may be configured to provide support depending on various dimensions of the elongated beam.

The supporting means may be configured to provide support along the elongated beam with a support position along the beam dependent on the deflection of the beam.

By making the support position dependent on the deflection of the beam, the pressure to flow dependency of the regulation may be fitted to a sought behaviour.

The support position along the beam may be continuously dependent on the degree of deflection of the beam. Thereby the pressure to flow dependency of the regulation may be continuously fitted to a sought behaviour.

The supporting means may be configured such that the support of the beam is moved towards the flow regulation passage upon deflection of the beam. Thereby the flow regulation passage is further throttled by the deflection of the beam and the position of the support of the beam cooperates with the deflection of the beam to reducing the cross-sectional area of the flow regulation passage in order to regulate the flow.

The supporting means is thus configured to effectively shorten the unsupported length of the elongated beam upon increasing deflection of the beam, thereby stiffening the beam. The higher the flow, the shorter the unsupported length of the beam and thereby an improved regulation.

The supporting means may comprise a ridge extending along the elongation of the beam and/or one or more discrete supports.

The supporting means may comprise a first and a second ridge extending along the elongation of the beam, and arranged at a first and a second lateral side of the beam (lateral meaning pertaining to the side). Thereby stable support of the lateral sides of the beam may be provided.

The first and second ridges may be curved, such that the position of the support along the elongated beam from the ridges is continuously dependent on the degree of deflection of the beam.

The supporting means may be symmetrical with respect to the first and second end portions of the elongated beam.

The elongated beam may have a length in the range of 5-20 mm, preferably 5-15 mm, and/or a width in the range of 2-10 mm, preferably 4-6 mm, and/or a thickness in the range of 10-500 μm, preferably 30-300 μm.

The flow channel may have a width in the range of 2-10 mm, preferably 4-6 mm, and/or a height in the range of 0.1-2 mm, preferably 0.5-1 mm.

The elongated beam may comprise silicon, germanium, silicon carbide, metal or a polymer material having a high level of fatigue strength, e.g. Polyimide, PEEK etc. Thereby the beam may be repeatedly bent with minimal risk of damage.

The invention further relates to a breath analysis device comprising a flow regulating device as disclosed herein for regulating a flow of exhaled breath to maintain a flow in the range of 10-300 ml/s, preferably maintaining a flow of 50±5 ml/s, and over a pressure range of 1000 Pa, preferably over 2000 Pa.

The breath analysis device may comprise a sensor for analysing nitric oxide, NO, content in exhaled breath.

The invention further relates to the use of a flow regulating device as disclosed herein in a breath analysis device for regulating a flow of exhaled breath to maintain a flow in the range of 10-300 ml/s, preferably maintaining a flow of 50±5 ml/s, and over a pressure range of 1000 Pa, preferably over 2000 Pa.

As used herein, the singular forms "a", "an" and "the" are intended to include plural forms as well, unless the context clearly indicates otherwise. The term about is defined to describe variations in the range of ±10%.

BRIEF DESCRIPTION OF DRAWINGS

The invention is now described, by way of example, with reference to the accompanying drawings, in which.

DESCRIPTION OF EMBODIMENTS

In the following, a detailed description of embodiments of the miniaturised fluid flow regulating device is described with reference to the drawings.

Figure 1:
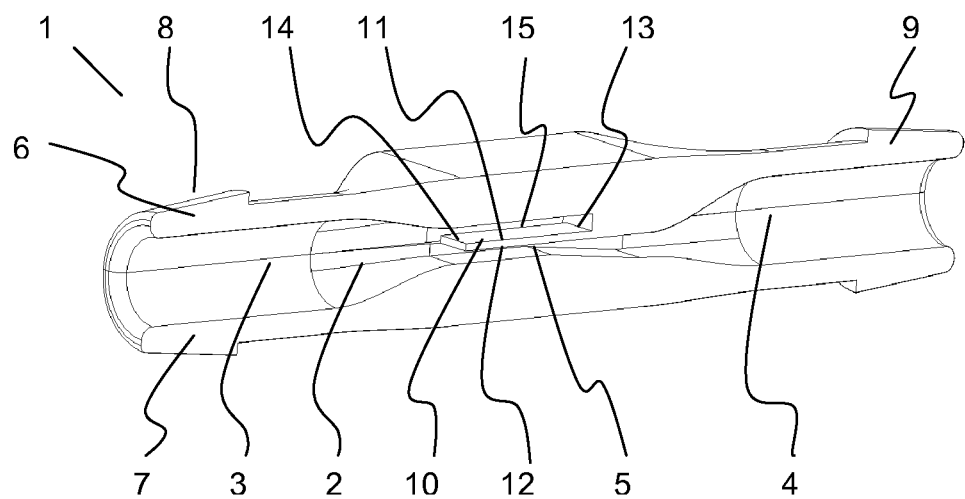
FIG. 1 shows a miniaturised fluid flow regulating device according to an embodiment, in a cut-away perspective view.

In FIG. 1 a miniaturised fluid flow regulating device 1 is shown, cut in half. The device comprises a fluid flow channel 2 with an inlet portion 3, an outlet portion 4 and a flow regulation passage 5 between the inlet portion and the outlet portion. The device is assembled by a first 6 and a second 7 part of material, forming a housing of the device. The material may e.g. be a polymer material. The device may comprise a first 8 and second 9 connector for connecting the device to e.g. tubing.

The flow regulating device comprises an elongated beam element 10 arranged in the flow channel 2 having the direction of elongation along the fluid flow channel. The elongated beam has a first end portion 13 and a second end portion 14 and extends between the inlet portion to the outlet portion of the flow channel.

The elongated beam comprises a first 11 and a second 12 face. The second face 12 of the elongated beam defines a wall in the flow regulation passage. The first end portion 13 of the beam is clamped in the device, e.g. by integrally forming the elongated beam in the same piece of material as the device itself or by rigid attachment to the material of the device. The second end portion 14 of the beam not supported, forming a free end. Thus, in this embodiment the beam is formed as a cantilever. A fluid space 15 is formed in the device communicating with the inlet portion of the fluid flow channel. The first face 11 of the elongated beam defines a wall in the fluid space. The fluid space is further delimited by the attachment of the first end 13 of the elongated beam.

In FIG. 1 the supporting means supporting the at least one of the first and second end portion are not shown.

Figure 2:
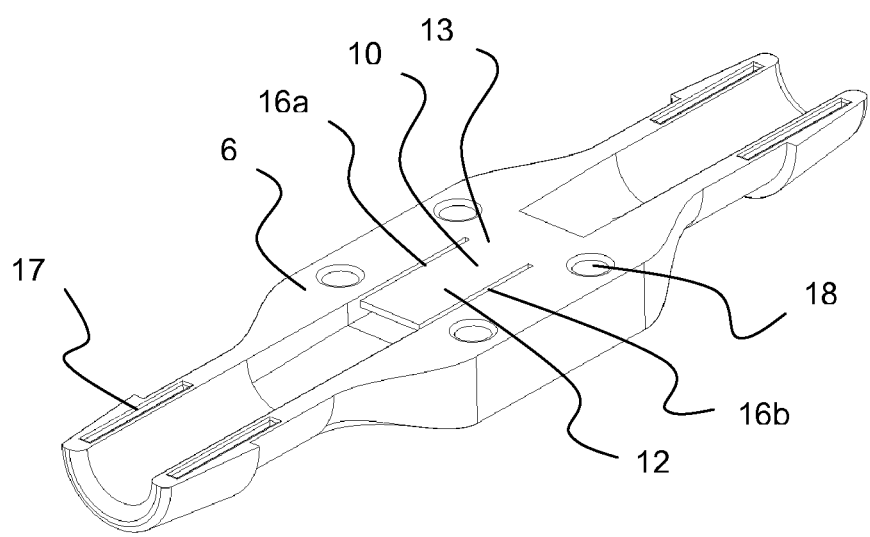
FIG. 2 shows part of a miniaturised fluid flow regulating device according to an embodiment, in perspective view.

In FIG. 2 the first part of material 6 forming part of the fluid regulating device is shown. The elongated beam 10 is now shown with the second face 12 facing the viewer. In this example the elongated beam is supported in the device by being integrally formed in the same piece of material as the first part 6. Thus the beam is clamped at the first end portion 13. The lateral sides of the beam (perpendicular to the elongation of the beam) are free to move, and thus slits 16a and 16b are formed along the sides of the elongated beam. These slits provides for a controlled but minimised leakage flow from the fluid space into the flow channel and towards the outlet portion of the flow channel. This leakage flow may be limited by designing the slits and e.g. by providing a ridge under and/or over the elongated beam to increase the pressure drop over the slits.

In FIG. 2 the supporting means supporting the at least one of the first and second end portion are not shown.

The first part of material 6 may be provided with protrusions 17 and/or indentions 18 to provide alignment and tight fitting of the first and second parts of material.

Figure 3:
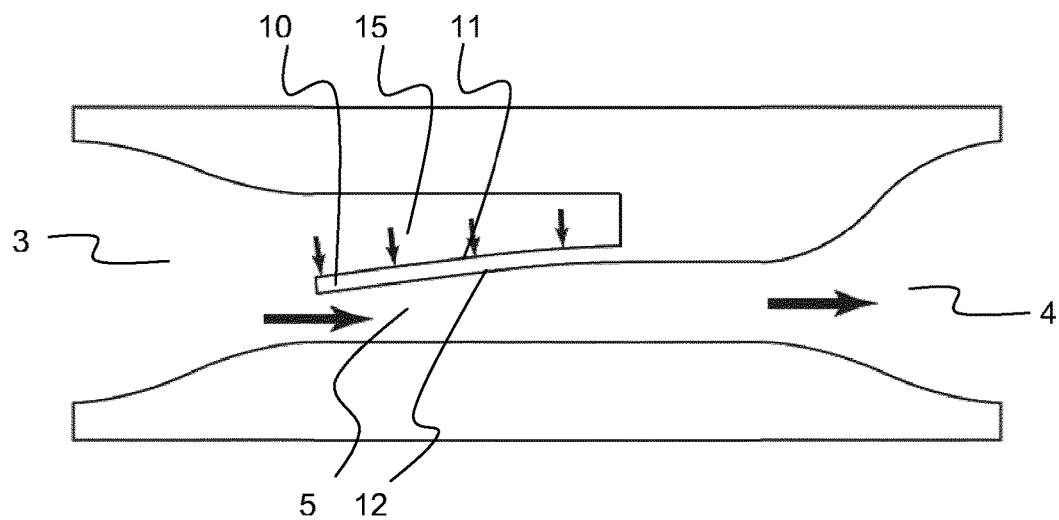
FIG. 3 shows a miniaturised fluid flow regulating device according to an embodiment, in a cross-sectional view.

FIG. 3 further shows the fluid regulating function of the device. The inlet portion 3, outlet portion 4 and flow regulation passage 5 of the flow channel is shown. From this drawing it is evident that the fluid space 15 is arranged such that the first face 11 of the beam 10 is subjected to fluid pressure communicating with the inlet portion 3 of the fluid flow channel. Thus a pressure difference acting on the first 11 and second 12 face of the elongated beam causes the beam element to bend and regulate fluid flow in the flow regulation passage. In particular, a higher pressure in the inlet portion (and thus the fluid space 15) than in the flow regulation passage 5 causes the elongated beam to bend towards the flow regulation passage to decrease the cross-sectional area of the flow regulation passage. Thereby the flow resistance in the flow regulation passage is increased, limiting the flow speed of the fluid passing the flow regulation passage.

In FIG. 3 the supporting means supporting the at least one of the first and second end portion are not shown.

Figure 4:
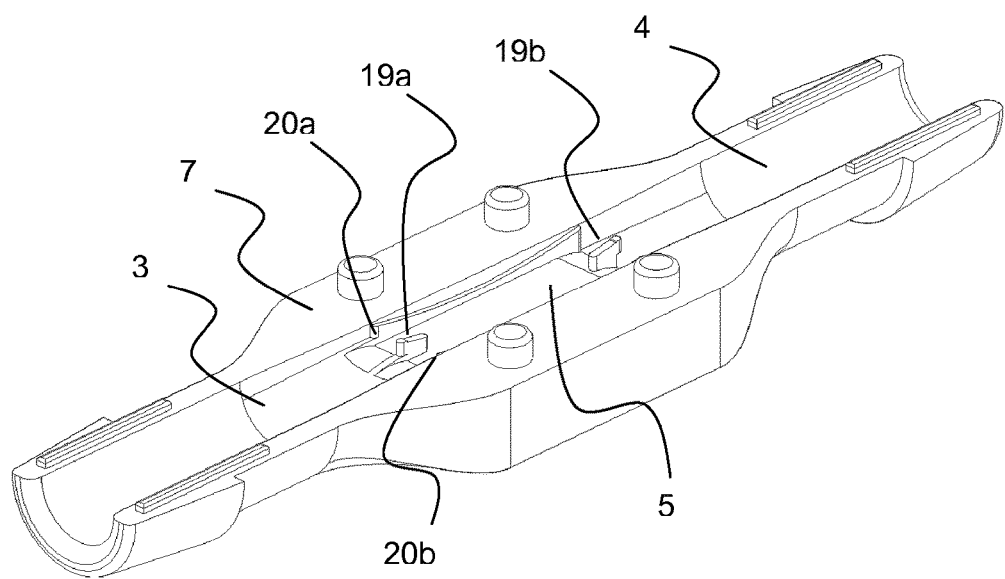
FIG. 4 shows part of a miniaturised fluid flow regulating device according to an embodiment, in perspective view.

In FIG. 4 an embodiment of a miniaturised fluid flow regulating device is shown. In FIG. 4 the configuration and support of the elongated beam is shown. FIG. 4 shows a part 7 of the device with an inlet portion 3, an outlet portion 4 and a flow regulation passage 5 between the inlet portion and the outlet portion. At the flow regulation passage a number of supporting means are provided to support an elongated beam element placed thereon (not shown). The supporting means comprises a first 19a and a second 19b discrete support arranged in the middle of the flow channel, towards the inlet and outlet portion respectively. Further, the supporting means comprises a first 20a and a second 20b ridge arranged along each side of the flow channel, to provide support along the lateral sides of the elongated beam. The ridges are also formed to limit the leak flow through slits formed between the elongated beam and lateral walls of the flow channel.

The ridge supports may be provided with a shape that provides support along the elongated beam upon deflection of the beam. The shape of the ridge may be such that the support position along the beam is continuously dependent on the deflection of the beam thereby effectively shortening the unsupported length of the elongated beam upon increasing deflection of the beam. This has the effect to stiffening the beam gradually (or stepwise) upon deflection.

Figure 5A:
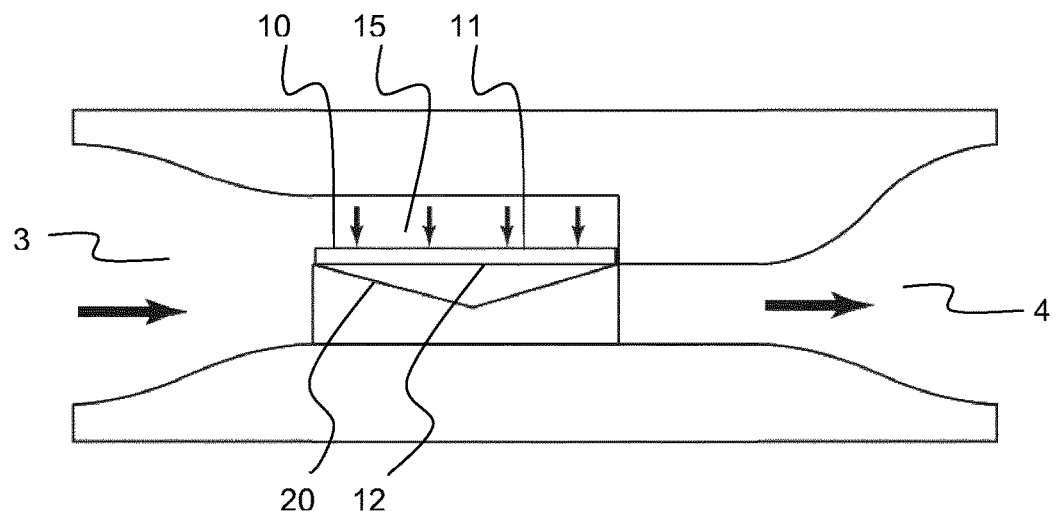
FIG. 5 shows a miniaturised fluid flow regulating device according to an embodiment, in a cross-sectional view.
Figure 5B:
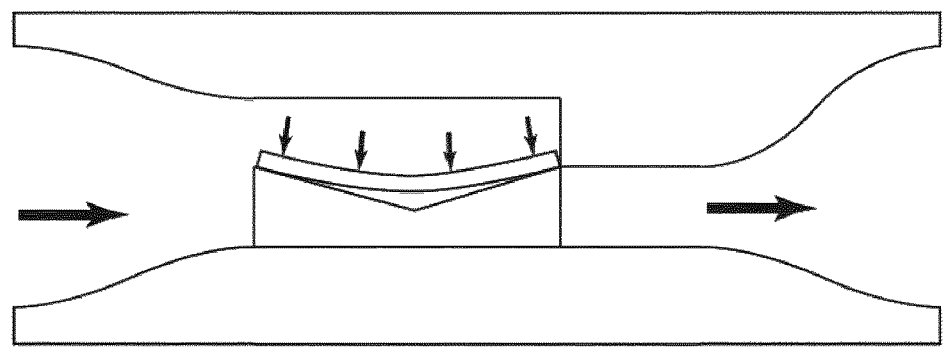
Figure 6:
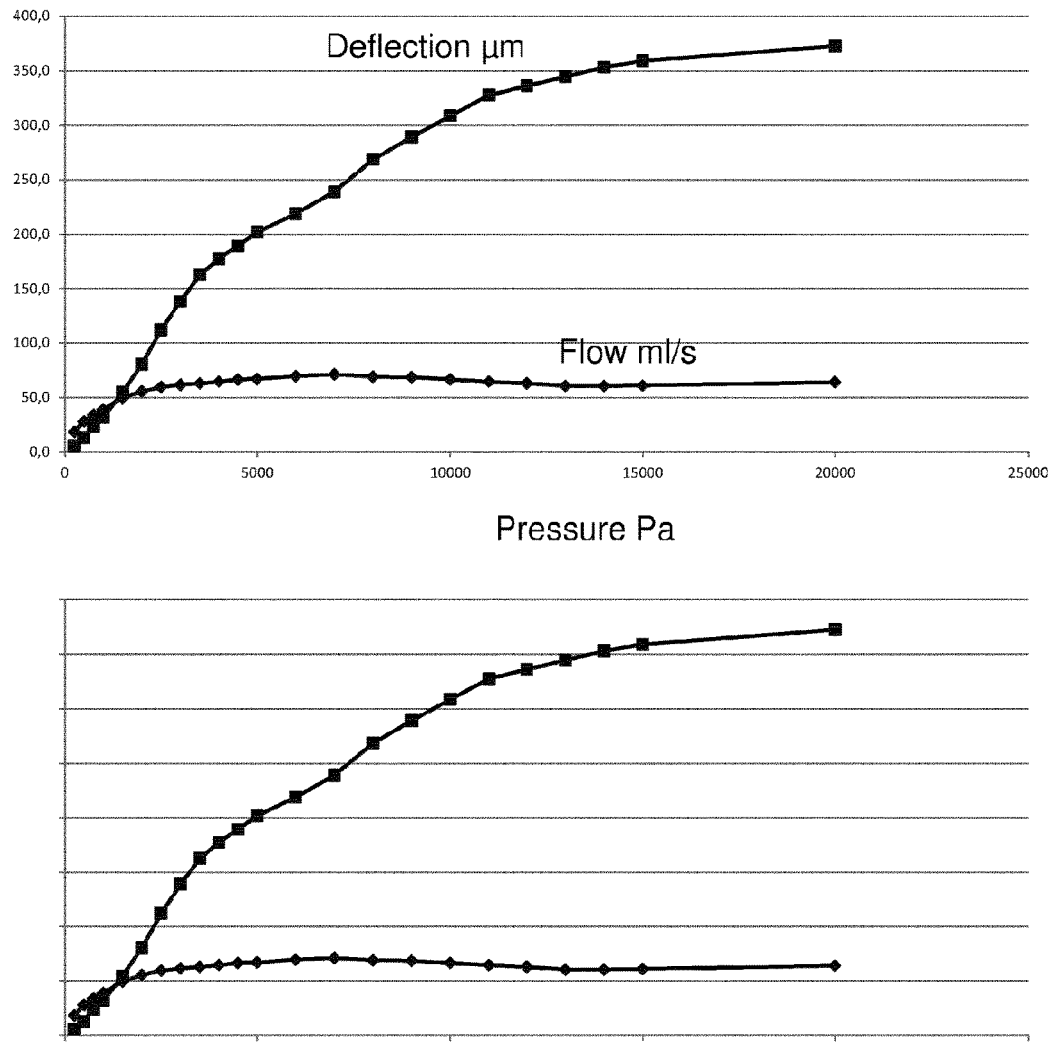
FIG. 6 shows the deflection of the beam element. It can be seen that the deflection of the beam element decreases, i.e. the beam element becomes harder and harder as the pressure increases. First 5000 Pa give a deflection of about 202 µm, further +5000 Pa gives +106 µm deflection, still further +5000 Pa gives +51 µm deflection, and yet still further +5000 Pa gives +12 µm deflection. The upper curve shows the deflection expressed in pm and the lower curve shows the resulting flow in ml/s. The scale is the same to the left.

In FIGS. 5a and 5b the operation of the device is shown. The fluid space 15 is arranged such that the first face 11 of the beam 10 is subjected to fluid pressure communicating with the inlet portion of the fluid flow channel. The elongated beam is simply supported on the supporting means comprising a ridge 20. A pressure difference acting on the first 11 and second 12 face of the elongated beam causes the beam element to bend and regulate fluid flow in the flow regulation passage.

In the example shown the ridge is V-shaped. This has the effect that the elongated beam initially is simply supported at the first and second end portion until the deflection of the beam is such that they tangent the V-shaped support (as shown in FIG. 5b). Thereafter any further deflection will result in the position of the support being moved towards the center of the V-shaped ridge. By moving the position of the support towards the center of the V-shaped ridge the effective length of the deflected beam will decrease, thereby increasing the stiffness of the beam.

The shape of the supporting means may thus be adapted to provide an increasing stiffness upon deflection, thus adapting the flow regulation in the flow regulation passage to a desired pressure-flow behavior. The supporting means may be in the form of a ridge having a V-shape, a gull-wing shape, a curved shape, a sinusoidal shape etc, or in the form of distributed discrete supports of different heights adapted to provide support upon increasing deflection.

The material of the beam may be selected to a material other than the material of the parts forming a housing, e.g. single crystalline silicon, metal etc. The material is preferably selected from a group of materials having a high fatigue strength.

The device comprises a cantilever that constitutes one of the walls in the flow regulation channel, as can be seen in FIG. 1. When a pressure is applied at the inlet, the inlet pressure will act along the full length of the first face of the cantilever. A flow in the narrow flow regulation channel beneath the cantilever will result in a pressure drop resulting in a net force distribution along the length of the cantilever, causing it to bend down and restrict the flow in the channel, as can be seen in FIG. 3.

The spring force of the cantilever (the elongated beam) effectively balances against the flow induced downward bending forces acting on it, resulting in a predictable deflection at any inlet pressure. In addition to the primary cantilever-controlled flow, a leak flow occurs which may be utilized to avoid too much flow restriction.

The total pressure drop in the device may be approximated and divided into three regions: a sudden contraction region where the flow meets the tip of the cantilever, a diffuser region along the length of the cantilever and a sudden expansion region at the exit, as shown FIG. 3. The total pressure drop caused by the cantilever restriction and the flow channel along the bottom of the cantilever may then be described by the following expression:

$$p_c = \Delta p_i + \Delta p_d + \Delta p_o$$

where $\Delta p_i$ is the inlet pressure drop caused by the sudden contraction of the flow channel, $\Delta p_d$ is the diffuser region pressure drop along the length of the cantilever and $\Delta p_o$ is the outlet pressure drop caused by sudden expansion of the flow channel.

The pressure drop at these regions may be approximated by the following expressions:

$$\Delta p_i = \xi_i \frac{\rho v_i}{2}; \quad \xi_i \approx 0.4$$

$$\Delta p_d = \xi_d \frac{\rho v_i}{2}; \quad \xi_d = 1 - \left(\frac{A_i}{A_0}\right)^2 - C_p$$

$$\Delta p_o = \xi_o \frac{\rho v_i}{2}; \quad \xi_o = \left(\frac{A_i}{A_0}\right)^2$$

where $\rho$ is the density of the fluid, $v_i$ is the mean flow velocity at the contracted inlet, $\xi_i$, $\xi_d$ and $\xi_o$ are pressure loss coefficients, $A_i$ and $A_0$ are cross sectional areas of the contracted inlet and the non-contracted channel respectively and $C_p$ is the pressure recovery coefficient.

Using Bernoulli's equation it can then be shown that the main flow may be approximated by the following expression:

$$\phi_c = \frac{\sqrt{p}}{B}\left(1 - \frac{C}{B^2}p\right)$$

where constants B and C are:

$$B = \sqrt{\frac{(1.4 - C_p)\rho}{2A_o^2}}$$

$$C = \frac{L^4\rho(21 - 4C_p)}{20Eb^2t^3h_0^3}$$

where L is the length of the cantilever, E is the elastic modulus, b and t are the width and thickness of the cantilever, respectively, and $h_0$ is the channel height at zero cantilever deflection.

The constants B and C may be optimized for a specific flow rate at two pressure levels using the following expressions:

$$B = \frac{\frac{P_2}{P_1} - 1}{\frac{\phi_1}{\phi_2}\left(\frac{P_2}{P_1}\right)^{3/2} - 1} \cdot \frac{\sqrt{P_2}}{\phi_2}$$

$$C = B^2\left(1 - \frac{B\phi_1}{\sqrt{P_1}}\right)\frac{1}{P_1}$$

where $P_1$ and $\phi_1$ are the pressure and flow rate, respectively, for the first target point and $P_2$ and $\phi_2$ are the pressure and flow rate for the second target point.

Assuming an ideal pressure source and no losses in the tubings connecting the device the total flow through the device may be approximated by:

$$\phi = \phi_c + \phi_l; \quad \phi_l \approx D\sqrt{p}$$

where $\phi_l$ is the leak flow and D is a constant defined by the geometry of the leak gaps.

The invention claimed is:

1. A miniaturised fluid flow regulating device comprising a fluid flow channel with an inlet portion, an outlet portion and a flow regulation passage between the inlet portion and the outlet portion, an elongated beam element arranged in the flow channel, such that a pressure difference over the inlet portion and the outlet portion causes the beam element to bend and regulate fluid flow in the flow regulation passage,
   wherein the elongated beam has a first end portion and a second end portion and extends from the inlet portion to the outlet portion of the flow channel,
   wherein the device comprises supporting means,
   wherein at least one of the first and second end portions are supported in the device by the supporting means, and
   wherein the supporting means is configured such that a position of support by the supporting means on the beam moves towards the flow regulation passage upon increased deflection of the beam.

2. The miniaturised fluid flow regulating device according to claim 1, wherein the supporting means is configured to effectively shorten the unsupported length of the elongated beam upon increasing deflection of the beam, thereby stiffening the beam.

3. The miniaturised fluid flow regulating device according to claim 1 wherein the supporting means comprises a ridge extending along the elongation of the beam.

4. The miniaturised fluid flow regulating device according to claim 1 wherein the supporting means comprises one or more discrete supports.

5. The miniaturised fluid flow regulating device according claim 1 wherein the supporting means comprises a first and a second ridge extending along the elongation of the beam, and arranged at a first and a second lateral side of the beam.

6. A miniaturised fluid flow regulating device comprising a fluid flow channel with an inlet portion, an outlet portion and a flow regulation passage between the inlet portion and the outlet portion, an elongated beam element arranged in the flow channel, such that a pressure difference over the inlet portion and the outlet portion causes the beam element to bend and regulate fluid flow in the flow regulation passage,
wherein the elongated beam has a first end portion and a second end portion and extends from the inlet portion to the outlet portion of the flow channel,
wherein the device comprises supporting means comprising a first and a second ridge extending along the elongation of the beam,
wherein at least one of the first and second end portions are supported in the device by the supporting means, and
wherein the first and second ridges are curved, such that the position of the support along the elongated beam from the ridges is continuously dependent on the degree of deflection of the beam.

7. The miniaturised fluid flow regulating device according to claim 6 wherein the elongated beam has a length in the range of 5-20 mm, preferably 5-15 mm, and/or a width in the range of 2-10 mm, preferably 4-6 mm, and/or a thickness in the range of 10-500 μm, preferably 30-300 μm.

8. The miniaturised fluid flow regulating device according to claim 6 wherein the flow channel has a width in the range of 2-10 mm, preferably 4-6 mm, and/or a height in the range of 0.1-2 mm, preferably 0.5-1 mm.

9. A breath analysis device comprising a miniaturised flow regulating device according to claim 6 for regulating a flow of exhaled breath to maintain a flow in the range of 10-300 ml/s, preferably maintaining a flow of 50±5 ml/s, and preferably over a pressure range of 1000 Pa.

10. The breath analysis device according to claim 9 comprising a sensor for analysing the concentration of nitric oxide, NO, in exhaled breath.

11. A method for regulating a flow of exhaled breath in a breath analysis device to maintain a flow in the range of 10-300 ml/s, over a pressure range of 1000 Pa, wherein the breath analysis device includes a fluid flow channel with an inlet portion, an outlet portion and a flow regulation passage between the inlet portion and the outlet portion, an elongated beam element arranged in the flow channel, such that a pressure difference over the inlet portion and the outlet portion causes the beam element to bend and regulate fluid flow in the flow regulation passage, wherein the elongated beam has a first end portion and a second end portion and extends from the inlet portion to the outlet portion of the flow channel, wherein the device comprises supporting means comprising a first and a second ridge extending along the elongation of the beam, wherein at least one of the first and second end portions are supported in the device by the supporting means, and wherein the first and second ridges are curved, such that the position of the support along the elongated beam from the ridges is continuously dependent on the degree of deflection of the beam, the method comprising:
deflecting the elongated beam toward the supporting means by pressure exerted by the flow of exhaled breath.

12. A method for regulating a flow of exhaled breath in a breath analysis device to maintain a flow of 50±5 ml/s over a pressure range of 1000 Pa, wherein the breath analysis device includes a fluid flow channel with an inlet portion, an outlet portion and a flow regulation passage between the inlet portion and the outlet portion, an elongated beam element arranged in the flow channel, such that a pressure difference over the inlet portion and the outlet portion causes the beam element to bend and regulate fluid flow in the flow regulation passage, wherein the elongated beam has a first end portion and a second end portion and extends from the inlet portion to the outlet portion of the flow channel, wherein the device comprises supporting means, wherein at least one of the first and second end portions are supported in the device by the supporting means, and wherein the supporting means is configured such that a position of support by the supporting means on the beam moves towards the flow regulation passage upon increased deflection of the beam, the method comprising:
deflecting the elongated beam toward the supporting means by pressure exerted by the flow of exhaled breath.

13. A breath analysis device comprising a miniaturised flow regulating device according to claim 1 for regulating a flow of exhaled breath to maintain a flow in the range of 10-300 ml/s, preferably maintaining a flow of 50±5 ml/s, and preferably over a pressure range of 1000 Pa.

14. The breath analysis device according to claim 13 comprising a sensor for analysing the concentration of nitric oxide, NO, in exhaled breath.

* * * * *